United States Patent [19]

Potter et al.

[11] Patent Number: 5,519,125
[45] Date of Patent: May 21, 1996

[54] PLANT ADENYLOSUCCINATE SYNTHETASE AND DNA CODING THEREFOR

[75] Inventors: Sharon L. Potter, Raleigh, N.C.; Eric R. Ward, Basel, Switzerland

[73] Assignee: Ciba-Geigy Corporation, Tarrytown, N.Y.

[21] Appl. No.: 361,611

[22] Filed: Dec. 22, 1994

[51] Int. Cl.$^6$ .......................... C12N 15/52; C12N 15/82; C12N 1/21; C12N 5/10
[52] U.S. Cl. ...................... 536/23.6; 536/23.2; 435/69.1; 435/70.1; 435/71.1; 435/172.3; 435/240.2; 435/240.4; 435/252.3; 435/254.2; 435/320.1
[58] Field of Search .................................. 536/23.2, 23.6; 435/69.1, 70.1, 71.1, 172.3, 240.2, 240.4, 252.3, 254.2, 320.1

[56] References Cited

PUBLICATIONS

Hatch, M. D. 1967. Phytochemistry 6(1): 115–119.

Aimi, J., et al., "Cloning of a cDNA Encoding Adenylosuccinate Lyase by Functional Complementation in *Escherichia coli*", *J. Biol. Chem.*, 265(16): 9011–9014 (1990).

Bass, M. B., et al., "Overproduction, Purification, and Characterization of Adenylosuccinate Synthetase from *Escherichia coli*", *Arch. Biochem. Biophys.* 256: 335–342 (1987).

Baugher, B. W., et al., "Changes in Isozymes of Adenylosuccinate Synthetase", *Biochem Biophy Res. Commun.* 94: 123–129 (1980).

D'Ovidio, R., et al., "Rapid and efficient detection of genetic polymorphism in wheat through amplification by polymerase chain reaction", *Plant Mol. Biol.* 15: 169–171 (1990).

Delauney, A. J., et al., "A soybean gene encoding $\Delta^1$-pyrroline-5-carboxylate reductase was isolated by functional complementation in *Escherichia coli* and is found to be osmoregulated", *Mol. Genet.* 221: 299–305 (1990).

Dorfman, B., "The Isolation of Adenylosuccinate Synthetase Mutants in Yeasst by Selection for Constitutive Behavior in Pigmented Strains", *Genetics* 61: 377–389 (1969).

Elledge, S. J., et al., "λYES: A multifunctional cDNA expression vector for the isolation of genes by complementation of yeast and *Escherichia coli* mutations," *Proc. Natl. Acad. Sci. USA* 88: 1731–1735 (1991).

Ellerström, M., et al., "Cloning of a cDNA for rape chloroplast 3–isopropylmalate dehydrogenase by genetic complementation in yeast", *Plant Mol. Biol.* 18: 557–566 (1992).

Frisch, D. A., et al., "Direct genetic selection of a maize cDNA for dihydrodipicolinate synthase in an *Escherichia coli dapA$^-$* auxotroph", *Mol. Gen. Genet.* 228: 287–293 (1991).

Guicherit, O. M., et al., "Amplification of an Adenylosuccinate Synthetase Gene in Alanosine–resistant Murine T–Lymphoma Cells", *J. of Biol. Chem.* 269(6): 4488–4496 (1994).

Guicherit, O. M., et al., "Molecular Cloning and Expression of a Mouse Muscle cDNA Encoding Adenylosuccinate Synthetase", *J. of Biol. Chem.* 266(33): 22582–22587 (1991).

Helentjaris, T., et al., "Restriction fragment polymorphisms as probes for plant diversity and their development as tools for applied plant breeding", *Plant Mol. Biol.* 5: 109–118 (1985).

Helentjaris, T., "A genetic linkage map for maize based on RFLPs", *Trends Genet.* 3(8): 217 (1987).

Kohorn, D. B. et al., "A Hydroprobic, Carboxy–Proximal Region of a Light–Harvesting Chlorophyll a/b Protein Is Necessary for Stable Integration into Thylakoid Membranes", *Plant Cell* 1: 159–166 (1989).

Lehninger, A. L., "The Biosynthesis of Nucleotides", *Biochemistry*, Worth Publishers, NY: p. 743 (1975).

Li, H., et al., "Information for Targeting to the Chloroplastic Inner Envelope Membrane is Contained in the Mature Region of the Maize Bt1–encoded Protein", *J. Biol. Chem.* 267: 18999–19004 (1992).

Li, H., et al., "Targeting of Proteins to the Outer Envelope Membrane Uses a Different Pathway than Transport into Chloroplasts", *Plant Cell* 3: 709–717 (1991).

Lowenstein, J. M., "The Purine Nucleotide Cycle Revised", *Int. J. Sports Med.* 11:S37–S46 (1990).

Mäntsälä, P., et al., "Cloning and Sequence of *Bacillus subtilis* purA and guaA, Involved in the Conversion of IMP to AMP and GMP", *J. of Bacter.*, 174(6): 1883–1890 (1992).

Minet, M., et al., "Complementation of *Saccharomyces cerevisiae* auxotrophic mutants by *Arabidopsis thaliana* cDNAs", *Plant J.* 2: 417–422 (1992).

Niyogi, K. K., et al., "Suppressors of trp1 Fluorescence Identify a New Arabidopsis Gene, TRP4, Encoding the Anthranilate Synthase β Subunit", *Plant Cell* 5: 1011–1027 (1993).

Poland, B. W., et al., "Crystal Structure of Adenylosuccinate Synthetase from *Escherichia coli*," *J. Biol. Chem.*, 268(34): 25334–25342 (1993).

Powell, S. M., et al., "Cloning and characterization of the cDNA encoding human adenylosuccinate synthetase", *FEBS* 303(1): 4–10 (1992).

Schnorr, K. M., et al., "Molecular characterization of the *Arabidopsis thaliana* cDNAs encoding three purine biosynthetic enzymes", *The Plant Journal*, 6(1): 113–121 (1994).

(List continued on next page.)

*Primary Examiner*—David T. Fox
*Attorney, Agent, or Firm*—James Scott Elmer

[57] ABSTRACT

The present invention provides novel plant DNA sequences coding for native adenylosuccinate synthetase (ADSS). Methods for using the complete or partial ADSS coding sequence as a probe for diagnostic, mapping and other purposes are taught. Generation of transformed host cells capable of expressing ADSS is also taught. Methods of using the transformed host cells are taught, including methods for recombinant production of ADSS enzymes. A method for using the plant ADSS enzyme to screen for inhibitors of ADSS activity is also provided.

9 Claims, No Drawings

OTHER PUBLICATIONS

Schubert, K. R., "Products of Biological Nitrogen Fixation in Higher Plants: Synthesis, Transport, and Metabolism", *Annu. Rev. Plant Physiol.* 37: 539–574 (1986).

Senecoff, J. F., et al., "Isolating the *Arabidopsis thaliana* Genes for de Novo Purine Synthesis by Suppression of *Escherichia coli* Mutants", *Plant Physiol.* 102: 387–399 (1993).

Snustad, D. P., et al., "Maize Glutamine Synthetase cDNAs: Isolation by Direct Genetic Selection in *Escherichia coli*", *Genetics* 120:1111–1124 (1988).

Sommer, S. S., et al., "PCR Amplification of Specific Alleles (PASA) is a General Method for Rapidly Detecting Known Single–Based Changes", *BioTechniques* 12(1): 82–87 (1992).

Stayton, M. M., et al., "Regulation, Genetics, and Properties of Adenylosuccinate Synthetase: A Review", *Curr. Top. Cell. Regul.* 22: 103–141 (1983).

Wiesmüller, L., et al., "Purification and cDNA–derived Sequence of Adenylosuccinate Synthetase from *Dictyostelium discoideum*", *J. of Biol. Chem.* 266(4): 2480–2485 (1991).

Wolfe, S. A., et al., "Nucleotide Sequence and Analysis of the purA Gene Encoding Adenylosuccinate Synthetase of *Escherichia coli* K12", *J. of Biol. Chem.* 263(35): 19147–19153 (1988).

PLANT ADENYLOSUCCINATE SYNTHETASE AND DNA CODING THEREFOR

FIELD OF THE INVENTION

The invention relates generally to an enzymatic activity involved in adenosine 5'-monophosphate biosynthesis in plants. In particular, the invention relates to the plant enzyme which catalyzes the synthesis of adenylosuccinate and the gene encoding this enzyme. In one aspect, the invention relates to the recombinant production of this enzyme in a heterologous host. In another aspect, the invention is applied to the identification of new herbicides. In yet another aspect, the invention relates to the development of genetic markers in plants.

BACKGROUND OF THE INVENTION

Adenosine 5'-monophosphate (AMP, also known as adenylic acid) is a precursor of adenosine 5'-triphosphate (ATP), the key energy carrying molecule for all living systems. The first committed enzymatic step in the biosynthesis of AMP is the synthesis of adenylosuccinate from inosine 5'-monophosphate (IMP; inosinic acid) and aspartate. The enzyme which catalyzes this step is known as adenylosuccinate synthetase (IMP:L-aspartate ligase(GDP-forming), EC 6.3.4.4, referred to herein as "ADSS").

In *E. coli*, ADSS is a dimer of identical 48 kD subunits. Its three-dimensional structure has been determined to 2.8 Å resolution (Poland et al., *J. Biol. Chem.* 268:25334–25342 (1993). In mammalian cells, the ADSS enzyme is present as two isoforms. An acidic form, present in non-muscle tissues, is thought to be involved in de novo production of AMP. A basic form, present in muscle tissue, thought to act as part of the purine nucleotide cycle, which involves interconversion of IMP and AMP with the net result of deaminating aspartate to fumarate (Lehninger, *Biochemistry*. Worth Publishers, N.Y. (1975), p. 743; Lowenstein, *Int. J. Sports Med.* 11:S36–S46 (1990).

Genes encoding the ADSS enzyme have been isolated from a variety of species including *E. coli* (Wolfe and Smith, J. Biol. Chem. 263:19147–19153 (1988)), *D. discoideum* (Weismuller et al., *J. Biol. Chem.* 266:2480–2485 (1991)), mouse (Guicherit et al., *J. Biol. Chem.* 266:22582–22587 (1991); Guicherit et al., *J. Biol. Chem.* 269:4488–4496 (1994), *Bacillus subtilus* (Maentsaelae and Zalkin, *J. Bacteriol.* 174:1881–1890 (1992), human (Powell et al., FEBS Lett. 303:4–10 (1992), *S. cerevisiae* (Genbank accession no. L22185), and *Caenorhabditis elegans* (EST; Genbank accession no. M75738). However, genes encoding the ADSS enzyme have heretofore not been isolated from any plant species.

Presently, too little is known about the plant ADSS enzyme and its relationship to the ADSS enzymes/genes which have been isolated from other organisms to allow isolation of ADSS encoding genes from any plant species using known approaches.

Methods for isolating genes which are based upon knowledge of the structure of the proteins they encode cannot be applied to plant ADSS genes because too little is presently known about plant ADSS enzymes. Metabolic enzymes such as ADSS are typically very difficult to purify from plants because of their extremely low abundance. In addition, the presence of various phenolic and carbohydrate compounds in plants can interfere with the isolation of pure enzyme with native activity.

In the absence of direct structural information, a number of standard techniques are available for the isolation of proteins and their corresponding genes. Such standard techniques include nucleic acid hybridization and amplification by polymerase chain reaction using oligonucleotide primers corresponding to conserved amino acid sequence motifs. Unfortunately, these techniques would not be expected to be useful for isolation of plant ADSS genes because they rely upon the presence of significant structural similarity (i.e. amino acid and DNA sequence) with known proteins and genes that have the same function. Since there is no significant structural similarity even among the known ADSS genes and proteins from non-plant organisms (see, e.g. Powell et al., *FEBS Lett.* 303:4–10 (1992)) it is unlikely that these proteins would share any significant structural similarity with plant ADSS proteins.

Another approach that has been used to isolate biosynthetic genes in other metabolic pathways from higher eukaryotes is the complementation of microbial mutants deficient in the activity of interest. For this approach, a library of cDNAs from the higher eukaryote is cloned in a vector that can direct expression of the cDNA in the microbial host. The vector is then transformed or otherwise introduced into the mutant microbe, and colonies are selected that are phenotypically no longer mutant.

This strategy has worked for isolating genes from higher eukaryotes that are involved in several metabolic pathways, including histidine biosynthesis (e.g. U.S. patent application Ser. No. 08/061,644 to Ward et al., incorporated by reference herein in its entirety), lysine biosynthesis (e.g. Frisch et al., *Mol. Gen. Genet.* 228:287 (1991)), purine biosynthesis (e.g. Aimi et al., *J. Biol. Chem.* 265:9011 (1990)), and tryptophan biosynthesis (e.g. Niyogi et al., *Plant Cell* 5: 1011 (1993)). This strategy has also been used to isolate plant genes including those coding for maize glutamine synthase (Snustad et al, *Genetics* 120:1111–1114 (1988)), soybean -pyrroline-5-carboxylate reductase (Delauney et al., *Mol. Genet.* 221:299–305 (1990), maize dihydrodipicolinate synthase (Frisch et al., *Mol. Gen. Genet.* 228:287–293(1991)), rape chloroplast 3-isopropylmalate dehydrogenase (Eller et al., *Plant Mol. Biol.* 18:557–566 (1992); *Proc. Natl. Acad. Sci, USA* 88:1731–1735 (1991)), and dihydroorotate dehydrogenase (Minet et al., *Plant J.* 2:417–422 (1992)).

Microbial mutants thought to be defective in ADSS activity are available (e.g. *E. coli* purA mutant designated CGCS 5408 and *E. coli* strains CGCS 4431 and 7039 from *E. coli* Genetic Stock Center, Yale Univ.; yeast ade12 mutants reported in Doffman, *Genetics* 6:377–389 (1969)). However, despite the availability of these mutants, application of the complementation technique to isolate cDNAs encoding ADS S enzymatic activity has proven to be unsuccessful for avian (Powell et al., *FEBS Lett.* 303:4–10 (1992)) and *B. subtilis* ADSS (Maentsaelae and Zalkin, *J. Bacteriol.* 174:1881–1890 (1992).

There are several reasons which may explain the failure of this complementation strategy when applied to ADSS, particularly eukaryotic ADSS genes. First, the eukaryotic ADSS cDNA sequence may not be expressed at adequate levels in the mutant microbe, for instance because of codon usage inconsistent with the usage preferences of the microbial host. Second, the primary translation product from the cloned eukaryotic coding sequence may not produce a functional polypeptide, for instance if activity requires a post-translational modification, such as glycosylation, that is not carried out by the microbe. Third, the heterologous protein expressed in *E. coli* may also be lethal to the cells in which it is expressed, thus rendering its isolation impossible.

Fourth, the eukaryotic protein may fail to assume its active conformation in the microbial host, for instance if the protein is normally targeted to a specific organellar membrane system that the microbial host specifically lacks. This last possibility is especially likely for the plant ADSS enzyme, which has been associated in the plant cell with organelles not present in microbial hosts used in the complementation assay (Schubert, *Annu. Rev. Plant Physiol.* 37:539–574 (1986), and presumably reaches that organellar system as a result of a post-translational targeting mechanism involving both an N-terminal transit sequence, and intrinsic properties of the mature polypeptide (see, e.g. Kohorn and Tobin, Plant Cell 1:159 (1989); Li et al., *Plant Cell* 3:709 (1991); Li et al., *J. Biol. Chem.* 267:18999 (1992)). Moreover, two other purine biosynthetic genes isolated from plants, 5'-phosphoribosyl-5-aminoimdazole synthetase (Senecoff and Meagher, *Plant Physiol.* 102:387–399 (1993)) and glycinamide synthetase (Schnorr et al., *Plant J.* 6:113–121 (1994)) also appear encode proteins that are targeted to the chloroplast.

SUMMARY OF THE INVENTION

The present invention provides an isolated DNA molecule encoding the adenylosuccinate synthetase (ADSS) enzyme from a plant source.

The DNA coding sequences for ADSS enzymes in *Arabidopsis thaliana* and *Zea mays* are provided in SEQ ID NOS: 1 and 3, respectively. Using the information provided by the present invention, the DNA coding sequence for the adenylosuccinate synthetase (ADSS) enzyme from any plant source may now be obtained using standard methods.

The present invention also encompasses the recombinant production of the ADSS enzyme, and methods for using recombinantly produced ADSS. In particular, the present invention provides methods of using purified ADSS to screen for novel herbicides which affect the activity of ADSS.

The present invention is further directed to probes and methods for detecting the presence and form of the ADSS gene and quantitating levels of ADSS transcripts in an organism. These methods may be used to diagnose disease conditions which are associated with an altered form of the ADSS enzyme or altered levels of expression of the ADSS enzyme.

DETAILED DESCRIPTION OF THE INVENTION

In one aspect, the present invention is directed to an isolated DNA molecule which encodes a eukaryotic form of adenylosuccinate synthetase (referred to herein as "ADSS"), the enzyme which catalyzes the synthesis of adenylosuccinate from IMP. The DNA coding sequence and corresponding amino acid sequence for an ADSS enzyme from *Arabidopsis thaliana* is provided as SEQ ID NOS: 1 and 2, respectively. The DNA coding sequence and corresponding amino acid sequence for a maize ADSS enzyme is provided as SEQ ID NOS:3 and 4, respectively.

The DNA encoding the ADSS enzyme may be isolated from the genome of any plant species desired according to the invention. One method taught for isolating a plant ADSS coding sequence is represented by Example 1. In this method cDNA clones encoding an ADSS enzyme are identified from a library of cDNA clones derived from the eukaryote of interest based on their ability to supply ADSS enzymatic activity to a mutant host organism deficient in this activity. Suitable host organisms for use in this method are those which can be used to screen cDNA expression libraries and for which mutants deficient in ADSS activity are either available or can be routinely generated. Such host organisms include, but are not limited to, *E. coli* and yeast.

Alternatively, plant ADSS coding sequences may be isolated according to well known techniques based on their sequence homology to the *Arabidopsis thaliana* (SEQ ID NO: 1) and *Zea mays* (SEQ ID NO: 3) ADSS coding sequences taught by the present invention. In these techniques all or part of the known ADSS coding sequence is used as a probe which selectively hybridizes to other ADSS coding sequences present in population of cloned genomic DNA fragments or cDNA fragments (i.e. genomic or cDNA libraries) from a chosen organism. Such techniques include hybridization screening of plated DNA libraries (either plaques or colonies; see, e.g. Sambrook et al., "Molecular Cloning", eds., Cold Spring Harbor Laboratory Press. (1989)) and amplification by PCR using oligonucleotide primers corresponding to sequence domains conserved among known ADSS amino acid sequences (see, e.g. Innis et al., "PCR Protocols, a Guide to Methods and Applications", pub. by Academic Press (1990)). These methods are particularly well suited to the isolation of ADSS coding sequences from organisms closely related to the organism from which the probe sequence is derived. Thus, application of these methods using the Arabidopsis or *Zea mays* coding sequence as a probe would be expected to be particularly well suited for the isolation of ADSS coding sequences from other plant species.

The isolated plant ADSS sequences taught by the present invention may be manipulated according to standard genetic engineering techniques to suit any desired purpose. For example, the entire ADSS sequence or portions thereof may be used as probes capable of specifically hybridizing to ADSS coding sequences and messenger RNAs. To achieve specific hybridization under a variety of conditions, such probes include sequences that are unique among ADSS coding sequences and are preferably at least 10 nucleotides in length, and most preferably at least 20 nucleotides in length. Such probes may be used to amplify and analyze ADSS coding sequences from a chosen organism via the well known process of polymerase chain reaction (PCR). This technique may be useful to isolate additional ADSS coding sequences from a desired organism or as a diagnostic assay to determine the presence of ADSS coding sequences in an organism. This technique may also be used to detect the presence of altered ADSS coding sequences in a plant associated with a particular condition of interest such as herbicide resistance, AMP deficiency, poor health, etc.

ADSS specific hybridization probes may also be used to map the location of the native ADSS gene(s) in the genome of a chosen plant using standard techniques based on the selective hybridization of the probe to genomic ADSS sequences. These techniques include, but are not limited to, identification of DNA polymorphisms identified or contained within the ADSS probe sequence, and use of such polymorphisms to follow segregation of the ADSS gene relative to other markers of known map position in a mapping population derived from self fertilization of a hybrid of two polymorphic parental lines (see e.g. Helentjaris et al., *Plant Mol. Biol.* 5:109 (1985); Sommer et al. *Biotechniques* 12:82 (1992); D'Ovidio et al., *Plant Mol. Biol.* 15:169 (1990)). While any plant ADSS sequence is contemplated to be useful as a probe for mapping ADSS genes, preferred probes are those ADSS sequences from plant species more closely related to the chosen plant species, and most preferred probes are those ADSS sequences from the chosen plant species. Mapping of ADSS genes in this manner is contemplated to be particularly useful for breeding purposes. For instance, by knowing the genetic map position of a mutant ADSS gene that confers herbicide resistance, flanking DNA markers can be identified from a reference genetic map (see, e.g., Helentjaris, *Trends Genet.* 3:217 (1987)). During introgression of the herbicide resistance trait into a new breeding line, these markers can then be used to monitor the extent of ADSS-linked flanking chromosomal DNA still present in the recurrent parent after each round of back-crossing.

ADSS specific hybridization probes may also be used to quantitate levels of ADSS mRNA in a plant using standard techniques such as Northern blot analysis. This technique may be useful as a diagnostic assay to detect altered levels of ADSS expression that may be associated with particular conditions such as deficiencies in adenylosuccinate or AMP levels or enhanced tolerance to herbicides which target ADSS.

For recombinant production of the enzyme in a host organism, the plant ADSS coding sequence may be inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189:113 (1986); Brosius, DNA 8:759 (1989)), yeast (see, e.g., Schneider and Guarente, *Meth. Enzymol.* 194:373 (1991)) and insect cells (see, e.g., Luckow and Summers, *Bio/Technol.* 6:47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pVl 11392/Sf21 cells (Invitrogen, La Jolla, Calif.).

Recombinantly produced plant ADSS enzyme can be isolated and purified using a variety of standard techniques. The actual techniques which may be used will vary depending upon the host organism used, whether the ADSS enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

Recombinantly produced plant ADSS enzyme is useful for a variety of purposes. For example, it may be used to supply ADSS enzymatic activity in vitro to synthesize adenylosuccinate. In vitro synthesis of adenylosuccinate may be accomplished by reacting IMP, GTP, and aspartate in the presence of ADSS enzyme in an appropriate buffer, containing a divalent cation such as $Mg^{2+}$ (see, e.g. Baugher et al. *Biochem. Biophys. Res. Commun.* 94:123–129 (1980); Stayton et al. *Curr. Top. Cell. Regul.* 22:103–141 (1983); Bass et al., *Arch. Biochem. Biophys.* 256:335–342 (1987)). The adenylosuccinate produced is a useful reagent which may be used as a substitute for purified adenylosuccinic acid previously available commercially from other sources.

Recombinantly produced plant ADSS enzyme may also be used in an in vitro assay to screen known herbicidal chemicals whose target has not been identified to determine if they inhibit ADSS. Such an in vitro assay may also be used as a more general screen to identify chemicals which inhibit ADSS activity and which are therefore herbicide candidates. Alternatively, recombinantly produced ADSS may be used to elucidate the complex structure of this enzyme. Such information regarding the structure of the ADSS enzyme may be used, for example, in the rational design of new inhibitory herbicides.

Typically, the inhibitory effect on ADSS is determined by a reduction or complete inhibition of adenylosuccinate synthesis in the in vitro assay (see, e.g. Baugher et al. *Biochem. Biophys. Res. Commun.* 94:123–129 (1980); Stayton et al. *Curr. Top. Cell. Regul.* 22:103–141 (1983); Bass et al., *Arch. Biochem. Biophys.* 256:335–342 (1987)). Such a determination may be made simply by comparing the amount of adenylosuccinate synthesized in the in vitro assay in the presence and absence of the candidate inhibitor.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual,* Cold Spring Harbor laboratory, Cold Spring Harbor, N.Y. (1982) and by T. J. Silhavy, M. L. Bennan, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

EXAMPLE 1

Isolation of Arabidopsis cDNAs encoding ADSS genes by functional complementation of an *E. coli* mutant.

An *Arabidopsis thaliana* (Landsberg) cDNA library in the plasmid vector pFL61 (Minet et al., *Plant J.* 2:417–422 (1992)) was obtained and amplified. The *E. coli* purA mutant PC0543 (CGSC #5408; *E. coli* Genetics Stock Center, Yale University, New Haven, Conn.) was obtained and maintained on N agar. The plasmid libraries were transformed into CGSC #5408 by electroporation using the Bio-Rad Gene Pulser and the manufacturer's conditions. The cells were plated on minimal E agar (Vogel and Bonner, *J. Biol. Chem.* 218:97–106 (1956) containing 100 mg/ml ampicillin and 0.4% casamino acids at a density of approximately 10,000,000 transformants/10 cm plate. Adenine prototrophs were recovered at a frequency of $1/6 \times 10^7$ from the pFL61 library. Plasmid DNA was isolated from the colony for sequence analysis. Purified plasmid DNA was shown to transform CGSC #5408 to purine prototrophy at high frequency. The purified plasmid complemented two additional *E. coli* purA mutants: ES4 (CGSC #4431; *E. coli* Genetics Stock Center, Yale University, New Haven, Conn.) and TX595 (CGSC #7039; *E. coli* Genetics Stock Center, Yale University, New Haven, Conn.), further confirming that it encoded a functional ADSS enzyme.

A restriction digest revealed that the cDNA insert was greater than 3 kB; sequence analysis revealed that the cDNA was chimeric, containing at the 3' end 1512 bp preceded by a polyA region. This 1512 bp region encodes an incomplete ADSS containing the mature protein sequence and a partial probable chloroplast transit peptide. A database search with the GAP program (Deveraux et al., *Nucleic Acids Res.* 12:387–395 (1984) reveals homology with the ADSS from *S. cerevisiae*. The two proteins are 70% similar, 51% identical with regions of high homology. The protein is 65% similar, 44% identical with *E. coli* ADSS.

ADSS-1, in the pBluescript SK vector, was deposited Sep. 22, 1994 as pWDC-6 (NRRL #B-21328).

The Arabidopsis cDNA sequence encoding ADSS-1 contained in pWDC-6 is set forth in SEQ ID NO: 1. The ADSS-1 amino acid sequence encoded by this cDNA is set forth in SEQ ID NO: 2.

EXAMPLE 2

Isolation of Maize cDNAs encoding ADSS genes based on sequence homology to Arabidopsis ADSS.

A custom-made Unizap *Zea Mays* (cv. Blizzard) cDNA library was purchased from Clontech. Approximately 160,000 pfu of the phage library was plated at a density of 8,000 plaques per 10 cm Petri dish, and duplicate filter lifts were made onto nitrocellulose membrane (Scheiller and Scheull) after approximately 7 hours growth at 37°. The filter lifts were probed with a PCR amplified fragment of the Arabidopsis ADSS cDNA labeled with $^{32}$P-dCTP by the random priming method (Life Technologies, Bethesda, Md.). Hybridization and wash conditions were at 50° as described in Church and Gilbert, 1984. After purification to single positively hybridizing plaques, plasmids were in vivo excised and cDNA inserts sequenced using dideoxy terminators labeled with fluorescent dyes (Applied Biosystems, Inc., Foster City, Calif.). The sequence thus obtained for the maize ADSS cDNA and the protein it encodes are provided as SEQ ID NOS: 3 and 4, respectively.

EXAMPLE 3

Isolation of additional ADSS genes based on sequence homology to known ADSS coding sequences A phage or plasmid library is plated at a density of approximately 10,000 plaques on a 10 cm Petri dish, and filter lifts of the plaques are made after overnight growth of the plates at 37° C. The plaque lifts are probed with one of the cDNAs set forth in SEQ ID NOS: 1 or 3, labeled with 32P-dCTP by the random priming method by means of a PrimeTime kit (International Biotechnologies, Inc., New Haven, Conn.). Hybridization conditions are 7% sodium dodecyl sulfate (SDS), 0.5M NaPO4 pH 7.0, 1 mM EDTA at 50° C. After hybridization overnight, the filters are washed with 2×SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain ADSS genes sequentially homologous to the known ADSS coding sequences from any other eukaryote, particularly other higher plant species.

An alignment of the predicted amino acid sequences of the respective proteins encoded by the nucleotide sequences shown in SEQ ID NOS: 1 and 3 are set forth in Table 1.

TABLE 1

Comparison of the Arabidopsis (SEQ ID NO:2) and Maize (SEQ ID NO:4) ADSS-1 Amino Acid Sequences

```
  1  MSLSSLTLDSNPRF AVGGPYHRRYPP LHHP RSFVSCS AKRPAVS ASLSVA  50  (SEQ ID NO: 2)
     | |||.|    |:|   |..|.  ...  :|:   . :.|.   ..|: |....|   |.
  1  MSLSTL...SHPAAAAAGSGKS LFPAGP AAQSVHFP KARLPVP AA...VS   44  (SEQ ID NO: 4)

51  ADSAATES LGRI GSLSQVSGVLGCQWGDEGKGKLVDI LAQHFDIVARCQG  100
     |..||... :|::|| .||||||||:|| |||||||||||:||.:||||||||
 45  AATAAVHAEDRVS SLTQVSGVLGS QWGDEGKGKLVDVLAP RFDIVARCQG   94

101  GANAGHTIYNSEGKKKFALHLVPSGILNEDTTCVI GNGVVVHLPGLFKEID  150
     ||||||||||||||||||||||||||||||:|:| ||:|||.|:|:||:| |||
 95  GANAGHTIYNSEGKKFALHLVPSGILHEGTLCVVGNGAV I HVPGFFGEID   144

151  GLESNGVS CKGRILVSDRAHLLFDFHQEVDGLRES ELAKSFIGTTKRGIG   200
     |||||||.|  ||||||||||||||||:|.||||||.||..|||||||||||
145  GLESNGVRCGGRILVSDRAHLLFDLHQAVDGLREAELENSFIGTTKRGIG   194

201  PAYSSKVI RNGI RVGDLRHMDTLP QKLDLLLS DAAARFQGFKYTP EMLRE  250
     |.||||.|||.:||.||||||||||.|.:|:..:|||:|..|::|
195  PCYSSKVTRNGLRVCDLRHMDTFGDKLDI LFK DAAS RFQGFQYSKSLLKE  244

251  EVEAYKRYADRLEPYITDTVHFINDSIS QKKKVLVEGGQATMLDIDFGTY  300
     ||| ||::||||||:|.||||.:|:||.||||:||||||||||||||||||
245  EVER YKKF ADRLEPFIADTVHVLNESIKQKKKI LVEGGQATMLDIDFGTY  294

301  PFVTSSSPSAGGICTGLGIAPS VVGDLIGVVKAYTTRVGSPFPTENLGT   350
     |||||||||||||||||||||..:|||||||||||.||||||||||| :|.
295  PFVTSSSPSAGGICTGLGIAPRAI GDLIGVVKAYTSRVGSPFPTELFGE   344

351  GGDLLRLAGQ EFGTTTGRPRRCGWLDIVALKF SCQINGFASLNLTKLDVL  400
     :|| || ||  ||||||||||||||| |||||||  ||||||.||||||||||
345  EGDRLRKAGMEFGTTTGRPRRCGWLDIVALKHSCQINGFS SLNLTKLDVL  394

401  SDLNEIQL GVAYKRSDGTP VKSFPGDLRLLEELHVE YEVLPGWKSDISSV  450
     |:|.||.:||.|...|| .:.|||||| ||:::|:|||||| .|||||
395  SGLS EIKVGVS YTQTDGQKL QSFPGDLDTLEQVQVNYEVLPGWQSDISSV  444
```

TABLE 1-continued

Comparison of the Arabidopsis (SEQ ID NO:2) and
Maize (SEQ ID NO:4) ADSS-1 Amino Acid Sequences

```
451  RNYS DLPKAAQQYVERIEELVGVPI HYIGI GPGRDALIYK*  491
     |.|.:||.||. ||||||||||||:|||:||||||||||
445  RRYDELPQAARL YVERIEELVGVPVHYIGVGPGRDALIYK*   485
```

Identical residues are denoted by the vertical bar between the two sequences. Alignment is performed using the GAP program described in Deveraux et al., Nucleic Acids Res. 12:387–395 (1984).

Various modifications of the invention described herein will become apparent to those skilled in the art. Such modifications are intended to fall within the scope of the appended claims.

---

We claim:

1. An isolated DNA molecule encoding a protein selected from the group consisting of an Arabidopsis adenylosuccinate synthetase(ADSS) and a maize ADSS.

2. The isolated DNA molecule of claim 1 wherein said Arabidopsis ADSS comprises the amino acid sequence set forth in SEQ ID NO: 2.

3. The isolated DNA molecule of claim 2 comprising the sequence set forth in SEQ ID NO: 1.

4. The isolated DNA molecule of claim 1 wherein said maize ADSS comprises the amino acid sequence set forth in SEQ ID NO: 4.

5. The isolated DNA molecule of claim 4 comprising the sequence set forth in SEQ ID NO: 3.

6. An expression cassette comprising a promoter operably linked to the DNA molecule of claim 1.

7. A recombinant vector comprising the expression cassette of claim 6, wherein said vector is capable of being stably transformed into a host cell.

8. A host cell stably transformed with the vector of claim 7, wherein said host cell is capable of expressing said DNA molecule.

9. A host cell of claim 8 selected from the group consisting of a bacterial cell, a yeast cell, and an insect cell.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1516 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..1470
        ( D ) OTHER INFORMATION: /product="Arabidopsis Adenylosuccinate Synthetase"

( x i ) SEQUENCE DESCRIPTION: SEQ ID NO:1:

```
ATG TCT CTC TCT TCC CTC ACT CTC GAC TCC AAT CCA AGA TTC GCT GTT           48
Met Ser Leu Ser Ser Leu Thr Leu Asp Ser Asn Pro Arg Phe Ala Val
 1               5                  10                  15

GGT GGA CCT TAT CAC CGC CGT TAT CCT CCT CTT CAC CAC CCT CGA AGC           96
Gly Gly Pro Tyr His Arg Arg Tyr Pro Pro Leu His His Pro Arg Ser
                20                  25                  30

TTC GTC TCT TGC TCT GCT AAA CGT CCA GCT GTC TCC GCT TCA CTG AGC          144
Phe Val Ser Cys Ser Ala Lys Arg Pro Ala Val Ser Ala Ser Leu Ser
            35                  40                  45

GTC GCC GCT GAT TCA GCC GCC ACT GAG TCT CTT GGA CGG ATT GGA TCA          192
Val Ala Ala Asp Ser Ala Ala Thr Glu Ser Leu Gly Arg Ile Gly Ser
        50                  55                  60

CTG AGT CAA GTA TCT GGT GTA CTC GGT TGC CAA TGG GGA GAT GAA GGT          240
Leu Ser Gln Val Ser Gly Val Leu Gly Cys Gln Trp Gly Asp Glu Gly
65                  70                  75                  80

AAA GGC AAA CTC GTT GAC ATC TTA GCC CAA CAC TTT GAC ATC GTT GCT          288
Lys Gly Lys Leu Val Asp Ile Leu Ala Gln His Phe Asp Ile Val Ala
                85                  90                  95

CGT TGT CAG GGT GGA GCT AAT GCT GGA CAC ACT ATA TAC AAT TCA GAG          336
Arg Cys Gln Gly Gly Ala Asn Ala Gly His Thr Ile Tyr Asn Ser Glu
                100                 105                 110

GGA AAG AAA TTT GCA CTT CAC CTT GTG CCT TCA GGT ATC CTG AAT GAG          384
Gly Lys Lys Phe Ala Leu His Leu Val Pro Ser Gly Ile Leu Asn Glu
            115                 120                 125

GAT ACT ACT TGT GTC ATT GGA AAC GGA GTT GTG GTG CAT TTG CCA GGT          432
Asp Thr Thr Cys Val Ile Gly Asn Gly Val Val Val His Leu Pro Gly
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 130 |     |     |     |     | 135 |     |     |     |     | 140 |     |     |      |
| CTC | TTC | AAA | GAG | ATT | GAT | GGT | TTG | GAG | TCC | AAT | GGT | GTC | TCC | TGT | AAA | 480  |
| Leu | Phe | Lys | Glu | Ile | Asp | Gly | Leu | Glu | Ser | Asn | Gly | Val | Ser | Cys | Lys |      |
| 145 |     |     |     |     | 150 |     |     |     |     | 155 |     |     |     |     | 160 |      |
| GGA | AGG | ATT | TTG | GTC | TCT | GAT | CGC | GCT | CAC | TTG | TTA | TTC | GAT | TTC | CAT | 528  |
| Gly | Arg | Ile | Leu | Val | Ser | Asp | Arg | Ala | His | Leu | Leu | Phe | Asp | Phe | His |      |
|     |     |     |     | 165 |     |     |     |     | 170 |     |     |     |     | 175 |     |      |
| CAA | GAG | GTT | GAT | GGG | CTC | AGG | GAA | TCT | GAG | CTT | GCC | AAG | TCG | TTC | ATT | 576  |
| Gln | Glu | Val | Asp | Gly | Leu | Arg | Glu | Ser | Glu | Leu | Ala | Lys | Ser | Phe | Ile |      |
|     |     |     | 180 |     |     |     |     | 185 |     |     |     |     | 190 |     |     |      |
| GGC | ACC | ACC | AAG | AGG | GGA | ATT | GGT | CCT | GCC | TAC | TCT | AGT | AAA | GTG | ATA | 624  |
| Gly | Thr | Thr | Lys | Arg | Gly | Ile | Gly | Pro | Ala | Tyr | Ser | Ser | Lys | Val | Ile |      |
|     |     | 195 |     |     |     |     | 200 |     |     |     |     | 205 |     |     |     |      |
| AGG | AAT | GGT | ATT | AGA | GTA | GGT | GAT | CTC | AGG | CAC | ATG | GAT | ACT | TTA | CCT | 672  |
| Arg | Asn | Gly | Ile | Arg | Val | Gly | Asp | Leu | Arg | His | Met | Asp | Thr | Leu | Pro |      |
|     | 210 |     |     |     |     | 215 |     |     |     |     | 220 |     |     |     |     |      |
| CAA | AAG | CTT | GAC | CTT | TTA | CTA | TCA | GAT | GCA | GCG | GCA | AGG | TTT | CAA | GGG | 720  |
| Gln | Lys | Leu | Asp | Leu | Leu | Leu | Ser | Asp | Ala | Ala | Ala | Arg | Phe | Gln | Gly |      |
| 225 |     |     |     |     | 230 |     |     |     |     | 235 |     |     |     |     | 240 |      |
| TTC | AAG | TAT | ACT | CCT | GAA | ATG | CTT | CGG | GAA | GAA | GTT | GAA | GCA | TAC | AAG | 768  |
| Phe | Lys | Tyr | Thr | Pro | Glu | Met | Leu | Arg | Glu | Glu | Val | Glu | Ala | Tyr | Lys |      |
|     |     |     |     | 245 |     |     |     |     | 250 |     |     |     |     | 255 |     |      |
| AGA | TAC | GCT | GAC | AGA | TTG | GAG | CCC | TAC | ATT | ACT | GAC | ACT | GTC | CAT | TTC | 816  |
| Arg | Tyr | Ala | Asp | Arg | Leu | Glu | Pro | Tyr | Ile | Thr | Asp | Thr | Val | His | Phe |      |
|     |     |     | 260 |     |     |     |     | 265 |     |     |     |     | 270 |     |     |      |
| ATC | AAT | GAC | TCG | ATT | TCG | CAG | AAG | AAA | AAG | GTT | TTG | GTC | GAA | GGT | GGT | 864  |
| Ile | Asn | Asp | Ser | Ile | Ser | Gln | Lys | Lys | Lys | Val | Leu | Val | Glu | Gly | Gly |      |
|     |     | 275 |     |     |     |     | 280 |     |     |     |     | 285 |     |     |     |      |
| CAA | GCT | ACA | ATG | TTG | GAC | ATT | GAC | TTT | GGG | ACT | TAT | CCT | TTT | GTT | ACT | 912  |
| Gln | Ala | Thr | Met | Leu | Asp | Ile | Asp | Phe | Gly | Thr | Tyr | Pro | Phe | Val | Thr |      |
|     | 290 |     |     |     |     | 295 |     |     |     |     | 300 |     |     |     |     |      |
| TCC | TCC | AGC | CCC | TCA | GCC | GGT | GGG | ATC | TGC | ACA | GGT | CTT | GGT | ATT | GCA | 960  |
| Ser | Ser | Ser | Pro | Ser | Ala | Gly | Gly | Ile | Cys | Thr | Gly | Leu | Gly | Ile | Ala |      |
| 305 |     |     |     |     | 310 |     |     |     |     | 315 |     |     |     |     | 320 |      |
| CCA | AGT | GTT | GTT | GGT | GAT | CTA | ATT | GGA | GTG | GTA | AAA | GCA | TAC | ACT | ACA | 1008 |
| Pro | Ser | Val | Val | Gly | Asp | Leu | Ile | Gly | Val | Val | Lys | Ala | Tyr | Thr | Thr |      |
|     |     |     |     | 325 |     |     |     |     | 330 |     |     |     |     | 335 |     |      |
| AGA | GTT | GGT | TCA | GGT | CCA | TTC | CCG | ACA | GAA | AAT | TTG | GGC | ACA | GGT | GGT | 1056 |
| Arg | Val | Gly | Ser | Gly | Pro | Phe | Pro | Thr | Glu | Asn | Leu | Gly | Thr | Gly | Gly |      |
|     |     |     | 340 |     |     |     |     | 345 |     |     |     |     | 350 |     |     |      |
| GAC | CTT | CTT | AGG | TTA | GCT | GGA | CAG | GAG | TTT | GGC | ACT | ACA | ACT | GGT | CGT | 1104 |
| Asp | Leu | Leu | Arg | Leu | Ala | Gly | Gln | Glu | Phe | Gly | Thr | Thr | Thr | Gly | Arg |      |
|     |     | 355 |     |     |     |     | 360 |     |     |     |     | 365 |     |     |     |      |
| CCT | CGT | CGG | TGT | GGC | TGG | CTT | GAC | ATT | GTT | GCC | CTG | AAA | TTT | TCT | TGC | 1152 |
| Pro | Arg | Arg | Cys | Gly | Trp | Leu | Asp | Ile | Val | Ala | Leu | Lys | Phe | Ser | Cys |      |
|     | 370 |     |     |     |     | 375 |     |     |     |     | 380 |     |     |     |     |      |
| CAA | ATC | AAT | GGA | TTT | GCA | TCA | CTT | AAT | CTC | ACT | AAG | CTT | GAT | GTA | CTT | 1200 |
| Gln | Ile | Asn | Gly | Phe | Ala | Ser | Leu | Asn | Leu | Thr | Lys | Leu | Asp | Val | Leu |      |
| 385 |     |     |     |     | 390 |     |     |     |     | 395 |     |     |     |     | 400 |      |
| TCG | GAT | CTG | AAC | GAA | ATC | CAG | CTG | GGT | GTG | GCT | TAC | AAG | AGG | AGT | GAC | 1248 |
| Ser | Asp | Leu | Asn | Glu | Ile | Gln | Leu | Gly | Val | Ala | Tyr | Lys | Arg | Ser | Asp |      |
|     |     |     |     | 405 |     |     |     |     | 410 |     |     |     |     | 415 |     |      |
| GGC | ACC | CCT | GTT | AAA | TCA | TTC | CCT | GGT | GAT | CTT | CGT | CTT | CTC | GAA | GAA | 1296 |
| Gly | Thr | Pro | Val | Lys | Ser | Phe | Pro | Gly | Asp | Leu | Arg | Leu | Leu | Glu | Glu |      |
|     |     |     | 420 |     |     |     |     | 425 |     |     |     |     | 430 |     |     |      |
| CTG | CAT | GTG | GAG | TAT | GAA | GTC | TTA | CCT | GGG | TGG | AAG | TCT | GAC | ATA | TCC | 1344 |
| Leu | His | Val | Glu | Tyr | Glu | Val | Leu | Pro | Gly | Trp | Lys | Ser | Asp | Ile | Ser |      |
|     |     | 435 |     |     |     |     | 440 |     |     |     |     | 445 |     |     |     |      |
| TCG | GTC | AGA | AAC | TAC | TCT | GAT | CTT | CCA | AAG | GCT | GCT | CAG | CAA | TAT | GTT | 1392 |
| Ser | Val | Arg | Asn | Tyr | Ser | Asp | Leu | Pro | Lys | Ala | Ala | Gln | Gln | Tyr | Val |      |

|     |     |     |     | 450 |     |     |     |     | 455 |     |     |     |     | 460 |     |      |
| --- | --- | --- | --- | --- | --- | --- | --- | --- | --- | --- | --- | --- | --- | --- | --- | ---- |
| GAG | AGG | ATT | GAA | GAA | CTC | GTG | GGT | GTG | CCC | ATT | CAT | TAC | ATT | GGT | ATT | 1440 |
| Glu | Arg | Ile | Glu | Glu | Leu | Val | Gly | Val | Pro | Ile | His | Tyr | Ile | Gly | Ile |      |
| 465 |     |     |     |     | 470 |     |     |     |     | 475 |     |     |     |     | 480 |      |

| GGG | CCC | GGT | CGT | GAT | GCC | CTT | ATA | TAT | AAA | TGATTTTTAG | TGTTAGGCTT | 1490 |
| --- | --- | --- | --- | --- | --- | --- | --- | --- | --- | --- | --- | --- |
| Gly | Pro | Gly | Arg | Asp | Ala | Leu | Ile | Tyr | Lys |            |            |      |
|     |     |     |     | 485 |     |     |     |     | 490 |            |            |      |

TTTTGGTTCC TCCACAAACT CAAAAT     1516

( 2 ) INFORMATION FOR SEQ ID NO:2:

( i ) SEQUENCE CHARACTERISTICS:
        ( A ) LENGTH: 490 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Leu | Ser | Ser | Leu | Thr | Leu | Asp | Ser | Asn | Pro | Arg | Phe | Ala | Val |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gly | Gly | Pro | Tyr | His | Arg | Arg | Tyr | Pro | Pro | Leu | His | His | Pro | Arg | Ser |
|     |     |     | 20  |     |     |     |     | 25  |     |     |     |     | 30  |     |     |
| Phe | Val | Ser | Cys | Ser | Ala | Lys | Arg | Pro | Ala | Val | Ser | Ala | Ser | Leu | Ser |
|     |     | 35  |     |     |     |     | 40  |     |     |     |     | 45  |     |     |     |
| Val | Ala | Ala | Asp | Ser | Ala | Ala | Thr | Glu | Ser | Leu | Gly | Arg | Ile | Gly | Ser |
|     | 50  |     |     |     |     | 55  |     |     |     |     | 60  |     |     |     |     |
| Leu | Ser | Gln | Val | Ser | Gly | Val | Leu | Gly | Cys | Gln | Trp | Gly | Asp | Glu | Gly |
| 65  |     |     |     |     | 70  |     |     |     |     | 75  |     |     |     |     | 80  |
| Lys | Gly | Lys | Leu | Val | Asp | Ile | Leu | Ala | Gln | His | Phe | Asp | Ile | Val | Ala |
|     |     |     |     | 85  |     |     |     |     | 90  |     |     |     |     | 95  |     |
| Arg | Cys | Gln | Gly | Gly | Ala | Asn | Ala | Gly | His | Thr | Ile | Tyr | Asn | Ser | Glu |
|     |     |     | 100 |     |     |     |     | 105 |     |     |     |     | 110 |     |     |
| Gly | Lys | Lys | Phe | Ala | Leu | His | Leu | Val | Pro | Ser | Gly | Ile | Leu | Asn | Glu |
|     |     | 115 |     |     |     |     | 120 |     |     |     |     | 125 |     |     |     |
| Asp | Thr | Thr | Cys | Val | Ile | Gly | Asn | Gly | Val | Val | Val | His | Leu | Pro | Gly |
|     | 130 |     |     |     |     | 135 |     |     |     |     | 140 |     |     |     |     |
| Leu | Phe | Lys | Glu | Ile | Asp | Gly | Leu | Glu | Ser | Asn | Gly | Val | Ser | Cys | Lys |
| 145 |     |     |     |     | 150 |     |     |     |     | 155 |     |     |     |     | 160 |
| Gly | Arg | Ile | Leu | Val | Ser | Asp | Arg | Ala | His | Leu | Leu | Phe | Asp | Phe | His |
|     |     |     |     | 165 |     |     |     |     | 170 |     |     |     |     | 175 |     |
| Gln | Glu | Val | Asp | Gly | Leu | Arg | Glu | Ser | Glu | Leu | Ala | Lys | Ser | Phe | Ile |
|     |     |     | 180 |     |     |     |     | 185 |     |     |     |     | 190 |     |     |
| Gly | Thr | Thr | Lys | Arg | Gly | Ile | Gly | Pro | Ala | Tyr | Ser | Ser | Lys | Val | Ile |
|     |     | 195 |     |     |     |     | 200 |     |     |     |     | 205 |     |     |     |
| Arg | Asn | Gly | Ile | Arg | Val | Gly | Asp | Leu | Arg | His | Met | Asp | Thr | Leu | Pro |
|     | 210 |     |     |     |     | 215 |     |     |     |     | 220 |     |     |     |     |
| Gln | Lys | Leu | Asp | Leu | Leu | Ser | Asp | Ala | Ala | Ala | Arg | Phe | Gln | Gly |     |
| 225 |     |     |     |     | 230 |     |     |     |     | 235 |     |     |     | 240 |     |
| Phe | Lys | Tyr | Thr | Pro | Glu | Met | Leu | Arg | Glu | Glu | Val | Glu | Ala | Tyr | Lys |
|     |     |     |     | 245 |     |     |     |     | 250 |     |     |     |     | 255 |     |
| Arg | Tyr | Ala | Asp | Arg | Leu | Glu | Pro | Tyr | Ile | Thr | Asp | Thr | Val | His | Phe |
|     |     |     | 260 |     |     |     |     | 265 |     |     |     |     | 270 |     |     |
| Ile | Asn | Asp | Ser | Ile | Ser | Gln | Lys | Lys | Lys | Val | Leu | Val | Glu | Gly | Gly |
|     |     | 275 |     |     |     |     | 280 |     |     |     |     | 285 |     |     |     |
| Gln | Ala | Thr | Met | Leu | Asp | Ile | Asp | Phe | Gly | Thr | Tyr | Pro | Phe | Val | Thr |
|     | 290 |     |     |     |     | 295 |     |     |     |     | 300 |     |     |     |     |

```
Ser  Ser  Ser  Pro  Ser  Ala  Gly  Gly  Ile  Cys  Thr  Gly  Leu  Gly  Ile  Ala
305            310                 315                           320

Pro  Ser  Val  Val  Gly  Asp  Leu  Ile  Gly  Val  Val  Lys  Ala  Tyr  Thr  Thr
                325                 330                           335

Arg  Val  Gly  Ser  Gly  Pro  Phe  Pro  Thr  Glu  Asn  Leu  Gly  Thr  Gly  Gly
                340                 345                           350

Asp  Leu  Leu  Arg  Leu  Ala  Gly  Gln  Glu  Phe  Gly  Thr  Thr  Thr  Gly  Arg
                355                 360                           365

Pro  Arg  Arg  Cys  Gly  Trp  Leu  Asp  Ile  Val  Ala  Leu  Lys  Phe  Ser  Cys
     370                      375                      380

Gln  Ile  Asn  Gly  Phe  Ala  Ser  Leu  Asn  Leu  Thr  Lys  Leu  Asp  Val  Leu
385                      390                 395                           400

Ser  Asp  Leu  Asn  Glu  Ile  Gln  Leu  Gly  Val  Ala  Tyr  Lys  Arg  Ser  Asp
                405                 410                           415

Gly  Thr  Pro  Val  Lys  Ser  Phe  Pro  Gly  Asp  Leu  Arg  Leu  Leu  Glu  Glu
                420                 425                           430

Leu  His  Val  Glu  Tyr  Glu  Val  Leu  Pro  Gly  Trp  Lys  Ser  Asp  Ile  Ser
          435                 440                      445

Ser  Val  Arg  Asn  Tyr  Ser  Asp  Leu  Pro  Lys  Ala  Ala  Gln  Gln  Tyr  Val
     450                      455                      460

Glu  Arg  Ile  Glu  Glu  Leu  Val  Gly  Val  Pro  Ile  His  Tyr  Ile  Gly  Ile
465                      470                 475                           480

Gly  Pro  Gly  Arg  Asp  Ala  Leu  Ile  Tyr  Lys
                485                 490
```

( 2 ) INFORMATION FOR SEQ ID NO:3:

( i ) SEQUENCE CHARACTERISTICS:
        ( A ) LENGTH: 1835 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 18..1469
        ( D ) OTHER INFORMATION: /product="Maize Adenylosuccinate Synthetase"

( x i ) SEQUENCE DESCRIPTION: SEQ ID NO:3:

```
AAAACCCTCC  CACCATC  ATG  TCG  CTC  TCC  ACA  CTC  AGC  CAC  CCG  GCC  GCC              50
                    Met  Ser  Leu  Ser  Thr  Leu  Ser  His  Pro  Ala  Ala
                                      495                      500

GCC  GCC  GCC  GGG  AGC  GGA  AAA  TCC  CTT  TTC  CCG  GCT  GGC  CCG  GCG  GCG         98
Ala  Ala  Ala  Gly  Ser  Gly  Lys  Ser  Leu  Phe  Pro  Ala  Gly  Pro  Ala  Ala
                505                      510                      515

CAG  TCC  GTA  CAT  TTC  CCC  AAG  GCA  CGG  CTC  CCT  GTC  CCC  GCC  GCC  GTC        146
Gln  Ser  Val  His  Phe  Pro  Lys  Ala  Arg  Leu  Pro  Val  Pro  Ala  Ala  Val
          520                      525                      530

TCC  GCC  GCT  ACT  GCG  GCT  GTT  CAC  GCG  GAG  GAT  AGG  GTT  TCG  TCG  CTG        194
Ser  Ala  Ala  Thr  Ala  Ala  Val  His  Ala  Glu  Asp  Arg  Val  Ser  Ser  Leu
     535                      540                      545

ACT  CAA  GTC  TCC  GGC  GTG  CTG  GGG  TCG  CAG  TGG  GGC  GAC  GAG  GGA  AAG        242
Thr  Gln  Val  Ser  Gly  Val  Leu  Gly  Ser  Gln  Trp  Gly  Asp  Glu  Gly  Lys
550                      555                      560                      565

GGC  AAG  CTC  GTC  GAC  GTG  CTC  GCC  CCC  CGC  TTC  GAC  ATA  GTC  GCG  CGT        290
Gly  Lys  Leu  Val  Asp  Val  Leu  Ala  Pro  Arg  Phe  Asp  Ile  Val  Ala  Arg
```

| | | | | | | | | | | | | | | | | |
|---|---|---|---|---|---|---|---|---|---|---|---|---|---|---|---|---|
| | | 570 | | | | | | 575 | | | | | | 580 | | |
| TGC | CAG | GGG | GGA | GCG | AAC | GCT | GGA | CAT | ACC | ATC | TAC | AAC | TCA | GAA | GGC | 338 |
| Cys | Gln | Gly | Gly | Ala | Asn | Ala | Gly | His | Thr | Ile | Tyr | Asn | Ser | Glu | Gly | |
| | | 585 | | | | | 590 | | | | | 595 | | | | |
| AAG | AAG | TTT | GCT | CTG | CAT | CTT | GTT | CCA | TCT | GGT | ATT | CTC | CAT | GAA | GGG | 386 |
| Lys | Lys | Phe | Ala | Leu | His | Leu | Val | Pro | Ser | Gly | Ile | Leu | His | Glu | Gly | |
| | | 600 | | | | 605 | | | | | 610 | | | | | |
| ACA | CTG | TGT | GTT | GTT | GGC | AAT | GGA | GCA | GTC | ATC | CAT | GTT | CCA | GGG | TTC | 434 |
| Thr | Leu | Cys | Val | Val | Gly | Asn | Gly | Ala | Val | Ile | His | Val | Pro | Gly | Phe | |
| | 615 | | | | 620 | | | | | 625 | | | | | | |
| TTT | GGA | GAA | ATT | GAT | GGT | CTT | GAG | TCC | AAT | GGA | GTC | CGC | TGC | GGT | GGA | 482 |
| Phe | Gly | Glu | Ile | Asp | Gly | Leu | Glu | Ser | Asn | Gly | Val | Arg | Cys | Gly | Gly | |
| 630 | | | | | 635 | | | | | 640 | | | | | 645 | |
| AGG | ATA | CTG | GTA | TCC | GAC | CGG | GCA | CAT | CTG | CTG | TTT | GAT | CTG | CAC | CAG | 530 |
| Arg | Ile | Leu | Val | Ser | Asp | Arg | Ala | His | Leu | Leu | Phe | Asp | Leu | His | Gln | |
| | | | | 650 | | | | 655 | | | | | 660 | | | |
| GCT | GTG | GAT | GGA | CTT | AGG | GAA | GCA | GAG | CTT | GAA | AAT | TCA | TTT | ATA | GGG | 578 |
| Ala | Val | Asp | Gly | Leu | Arg | Glu | Ala | Glu | Leu | Glu | Asn | Ser | Phe | Ile | Gly | |
| | | | 665 | | | | | 670 | | | | | 675 | | | |
| ACA | ACT | AAG | AGA | GGC | ATT | GGT | CCT | TGT | TAC | TCC | AGC | AAG | GTA | ACT | CGA | 626 |
| Thr | Thr | Lys | Arg | Gly | Ile | Gly | Pro | Cys | Tyr | Ser | Ser | Lys | Val | Thr | Arg | |
| | | | 680 | | | | | 685 | | | | | 690 | | | |
| AAT | GGA | CTG | CGG | GTT | TGT | GAT | TTA | CGA | CAC | ATG | GAC | ACT | TTT | GGG | GAT | 674 |
| Asn | Gly | Leu | Arg | Val | Cys | Asp | Leu | Arg | His | Met | Asp | Thr | Phe | Gly | Asp | |
| | 695 | | | | | 700 | | | | | 705 | | | | | |
| AAG | CTT | GAC | ATC | TTA | TTC | AAA | GAC | GCT | GCT | TCG | AGA | TTT | CAA | GGC | TTT | 722 |
| Lys | Leu | Asp | Ile | Leu | Phe | Lys | Asp | Ala | Ala | Ser | Arg | Phe | Gln | Gly | Phe | |
| 710 | | | | | 715 | | | | | 720 | | | | | 725 | |
| CAG | TAC | AGC | AAA | AGC | TTG | CTC | AAG | GAA | GAG | GTT | GAG | AGA | TAC | AAG | AAG | 770 |
| Gln | Tyr | Ser | Lys | Ser | Leu | Leu | Lys | Glu | Glu | Val | Glu | Arg | Tyr | Lys | Lys | |
| | | | | 730 | | | | | 735 | | | | | 740 | | |
| TTT | GCT | GAT | CGC | TTG | GAG | CCC | TTC | ATT | GCT | GAT | ACC | GTG | CAT | GTG | CTA | 818 |
| Phe | Ala | Asp | Arg | Leu | Glu | Pro | Phe | Ile | Ala | Asp | Thr | Val | His | Val | Leu | |
| | | | 745 | | | | | 750 | | | | | 755 | | | |
| AAT | GAA | TCT | ATC | AAG | CAG | AAG | AAG | AAA | ATC | CTG | GTC | GAA | GGC | GGC | CAA | 866 |
| Asn | Glu | Ser | Ile | Lys | Gln | Lys | Lys | Lys | Ile | Leu | Val | Glu | Gly | Gly | Gln | |
| | | 760 | | | | | 765 | | | | | 770 | | | | |
| GCA | ACT | ATG | CTG | GAT | ATT | GAT | TTT | GGC | ACT | TAT | CCA | TTT | GTG | ACT | TCT | 914 |
| Ala | Thr | Met | Leu | Asp | Ile | Asp | Phe | Gly | Thr | Tyr | Pro | Phe | Val | Thr | Ser | |
| | 775 | | | | | 780 | | | | | 785 | | | | | |
| TCT | AGC | CCT | TCA | GCT | GGC | GGG | ATA | TGC | ACA | GGC | CTA | GGG | ATT | GCT | CCA | 962 |
| Ser | Ser | Pro | Ser | Ala | Gly | Gly | Ile | Cys | Thr | Gly | Leu | Gly | Ile | Ala | Pro | |
| 790 | | | | | 795 | | | | | 800 | | | | | 805 | |
| AGG | GCA | ATT | GGC | GAC | CTG | ATT | GGA | GTG | GTC | AAA | GCT | TAC | ACA | TCT | AGA | 1010 |
| Arg | Ala | Ile | Gly | Asp | Leu | Ile | Gly | Val | Val | Lys | Ala | Tyr | Thr | Ser | Arg | |
| | | | 810 | | | | | 815 | | | | | 820 | | | |
| GTC | GGC | TCT | GGC | CCT | TTC | CCA | ACT | GAA | CTA | TTT | GGA | GAG | GAA | GGT | GAT | 1058 |
| Val | Gly | Ser | Gly | Pro | Phe | Pro | Thr | Glu | Leu | Phe | Gly | Glu | Glu | Gly | Asp | |
| | | | 825 | | | | | 830 | | | | | 835 | | | |
| CGC | CTT | AGG | AAA | GCT | GGA | ATG | GAA | TTT | GGC | ACA | ACA | ACA | GGT | CGC | CCA | 1106 |
| Arg | Leu | Arg | Lys | Ala | Gly | Met | Glu | Phe | Gly | Thr | Thr | Thr | Gly | Arg | Pro | |
| | | | 840 | | | | | 845 | | | | | 850 | | | |
| AGG | CGT | TGC | GGC | TGG | CTT | GAC | ATT | GTT | GCG | CTT | AAG | CAC | AGC | TGC | CAA | 1154 |
| Arg | Arg | Cys | Gly | Trp | Leu | Asp | Ile | Val | Ala | Leu | Lys | His | Ser | Cys | Gln | |
| | 855 | | | | | 860 | | | | | 865 | | | | | |
| ATC | AAT | GGG | TTC | TCA | TCA | CTT | AAT | CTG | ACC | AAA | CTG | GAT | GTT | CTG | TCC | 1202 |
| Ile | Asn | Gly | Phe | Ser | Ser | Leu | Asn | Leu | Thr | Lys | Leu | Asp | Val | Leu | Ser | |
| 870 | | | | | 875 | | | | | 880 | | | | | 885 | |
| GGG | TTG | TCA | GAA | ATT | AAG | GTG | GGT | GTT | TCT | TAT | ACC | CAG | ACT | GAT | GGA | 1250 |
| Gly | Leu | Ser | Glu | Ile | Lys | Val | Gly | Val | Ser | Tyr | Thr | Gln | Thr | Asp | Gly | |

|   |   |   |   |   |   |   |   |   |   |   | | | | | |
|---|---|---|---|---|---|---|---|---|---|---|---|---|---|---|---|
| | | | | 890 | | | | | 895 | | | | | 900 | |
| CAG | AAG | CTG | CAA | TCC | TTC | CCT | GGG | GAT | CTT | GAT | ACC | CTT | GAG | CAA | GTA | 1298
| Gln | Lys | Leu | Gln | Ser | Phe | Pro | Gly | Asp | Leu | Asp | Thr | Leu | Glu | Gln | Val |
| | | | 905 | | | | | 910 | | | | | 915 | | |
| CAG | GTC | AAC | TAT | GAG | GTT | CTG | CCT | GGG | TGG | CAA | AGT | GAC | ATT | TCT | TCT | 1346
| Gln | Val | Asn | Tyr | Glu | Val | Leu | Pro | Gly | Trp | Gln | Ser | Asp | Ile | Ser | Ser |
| | | 920 | | | | | 925 | | | | | 930 | | | |
| GTT | CGA | AGA | TAC | GAT | GAA | CTT | CCC | CAA | GCT | GCC | CGC | CTC | TAT | GTG | GAG | 1394
| Val | Arg | Arg | Tyr | Asp | Glu | Leu | Pro | Gln | Ala | Ala | Arg | Leu | Tyr | Val | Glu |
| | 935 | | | | | 940 | | | | | 945 | | | | |
| AGG | ATA | GAA | GAA | CTT | GTT | GGT | GTT | CCC | GTG | CAC | TAC | ATT | GGT | GTT | GGA | 1442
| Arg | Ile | Glu | Glu | Leu | Val | Gly | Val | Pro | Val | His | Tyr | Ile | Gly | Val | Gly |
| 950 | | | | | 955 | | | | | 960 | | | | | 965 |
| CCT | GGC | AGA | GAT | GCT | CTC | ATA | TAC | AAG | TAAAAGCAAC | | | TTTATTGGT | | | | 1489
| Pro | Gly | Arg | Asp | Ala | Leu | Ile | Tyr | Lys | | | | | | | |
| | | | 970 | | | | | | | | | | | | |

```
CCTTGGTTGG  GCGGAAACCT  GGCCGGGACT  CGGGAGCATT  TGCATTTTCT  TGGCGTGGTA     1549

GCTTTTGATA  CGGTGAAGTC  ACTGACTCGT  GGAGTGATGT  TGCTCAATAA  TCAGAACCTT     1609

GTTCTAATAC  AGCCGCTGAG  ACATCAGCTA  AGGCGAATAA  GGGAAGGATG  AGTCATTTGC     1669

ACCATGTTTG  ACCACCAATT  GTTAGGTGGT  CCATATATTT  TGTACTAATT  GTGAGACTTT     1729

GTGCTATGGA  TCTCAACTGT  ATACCTTGCT  GGTGCATGGC  TTTGGGTTTA  CATGGTTGAA     1789

AATGAGATTG  GTGTACTAAT  TGTCTAAAAA  AAAAAAAAA   AAAAAA                     1835
```

( 2 ) INFORMATION FOR SEQ ID NO:4:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ser | Leu | Ser | Thr | Leu | Ser | His | Pro | Ala | Ala | Ala | Ala | Ala | Gly | Ser |
|---|---|---|---|---|---|---|---|---|---|---|---|---|---|---|---|
| 1 | | | | 5 | | | | | 10 | | | | | 15 | |
| Gly | Lys | Ser | Leu | Phe | Pro | Ala | Gly | Pro | Ala | Ala | Gln | Ser | Val | His | Phe |
| | | | 20 | | | | | 25 | | | | | 30 | | |
| Pro | Lys | Ala | Arg | Leu | Pro | Val | Pro | Ala | Ala | Val | Ser | Ala | Ala | Thr | Ala |
| | | 35 | | | | | 40 | | | | | 45 | | | |
| Ala | Val | His | Ala | Glu | Asp | Arg | Val | Ser | Ser | Leu | Thr | Gln | Val | Ser | Gly |
| | 50 | | | | | 55 | | | | | 60 | | | | |
| Val | Leu | Gly | Ser | Gln | Trp | Gly | Asp | Glu | Gly | Lys | Gly | Lys | Leu | Val | Asp |
| 65 | | | | | 70 | | | | | 75 | | | | | 80 |
| Val | Leu | Ala | Pro | Arg | Phe | Asp | Ile | Val | Ala | Arg | Cys | Gln | Gly | Gly | Ala |
| | | | | 85 | | | | | 90 | | | | | 95 | |
| Asn | Ala | Gly | His | Thr | Ile | Tyr | Asn | Ser | Glu | Gly | Lys | Lys | Phe | Ala | Leu |
| | | | 100 | | | | | 105 | | | | | 110 | | |
| His | Leu | Val | Pro | Ser | Gly | Ile | Leu | His | Glu | Gly | Thr | Leu | Cys | Val | Val |
| | | 115 | | | | | 120 | | | | | 125 | | | |
| Gly | Asn | Gly | Ala | Val | Ile | His | Val | Pro | Gly | Phe | Phe | Gly | Glu | Ile | Asp |
| | 130 | | | | | 135 | | | | | 140 | | | | |
| Gly | Leu | Glu | Ser | Asn | Gly | Val | Arg | Cys | Gly | Gly | Arg | Ile | Leu | Val | Ser |
| 145 | | | | | 150 | | | | | 155 | | | | | 160 |
| Asp | Arg | Ala | His | Leu | Leu | Phe | Asp | Leu | His | Gln | Ala | Val | Asp | Gly | Leu |
| | | | | 165 | | | | | 170 | | | | | 175 | |
| Arg | Glu | Ala | Glu | Leu | Glu | Asn | Ser | Phe | Ile | Gly | Thr | Thr | Lys | Arg | Gly |

|     |     | 180 |     |     |     |     | 185 |     |     |     |     | 190 |     |     |
|-----|-----|-----|-----|-----|-----|-----|-----|-----|-----|-----|-----|-----|-----|-----|
| Ile | Gly | Pro 195 | Cys | Tyr | Ser | Ser | Lys 200 | Val | Thr | Arg | Asn | Gly 205 | Leu | Arg | Val |
| Cys | Asp 210 | Leu | Arg | His | Met | Asp 215 | Thr | Phe | Gly | Asp | Lys 220 | Leu | Asp | Ile | Leu |
| Phe 225 | Lys | Asp | Ala | Ala | Ser 230 | Arg | Phe | Gln | Gly | Phe 235 | Gln | Tyr | Ser | Lys | Ser 240 |
| Leu | Leu | Lys | Glu | Glu 245 | Val | Glu | Arg | Tyr | Lys 250 | Lys | Phe | Ala | Asp | Arg 255 | Leu |
| Glu | Pro | Phe | Ile 260 | Ala | Asp | Thr | Val | His 265 | Val | Leu | Asn | Glu | Ser 270 | Ile | Lys |
| Gln | Lys | Lys 275 | Lys | Ile | Leu | Val | Glu 280 | Gly | Gly | Gln | Ala | Thr 285 | Met | Leu | Asp |
| Ile | Asp 290 | Phe | Gly | Thr | Tyr | Pro 295 | Phe | Val | Thr | Ser | Ser 300 | Ser | Pro | Ser | Ala |
| Gly 305 | Gly | Ile | Cys | Thr | Gly 310 | Leu | Gly | Ile | Ala | Pro 315 | Arg | Ala | Ile | Gly | Asp 320 |
| Leu | Ile | Gly | Val | Val 325 | Lys | Ala | Tyr | Thr | Ser 330 | Arg | Val | Gly | Ser | Gly 335 | Pro |
| Phe | Pro | Thr | Glu 340 | Leu | Phe | Gly | Glu | Glu 345 | Gly | Asp | Arg | Leu | Arg 350 | Lys | Ala |
| Gly | Met | Glu 355 | Phe | Gly | Thr | Thr | Thr 360 | Gly | Arg | Pro | Arg | Arg 365 | Cys | Gly | Trp |
| Leu | Asp 370 | Ile | Val | Ala | Leu | Lys 375 | His | Ser | Cys | Gln | Ile 380 | Asn | Gly | Phe | Ser |
| Ser 385 | Leu | Asn | Leu | Thr | Lys 390 | Leu | Asp | Val | Leu | Ser 395 | Gly | Leu | Ser | Glu | Ile 400 |
| Lys | Val | Gly | Val | Ser 405 | Tyr | Thr | Gln | Thr | Asp 410 | Gly | Gln | Lys | Leu | Gln 415 | Ser |
| Phe | Pro | Gly | Asp 420 | Leu | Asp | Thr | Leu | Glu 425 | Gln | Val | Gln | Val | Asn 430 | Tyr | Glu |
| Val | Leu | Pro 435 | Gly | Trp | Gln | Ser | Asp 440 | Ile | Ser | Ser | Val | Arg 445 | Arg | Tyr | Asp |
| Glu | Leu 450 | Pro | Gln | Ala | Ala | Arg 455 | Leu | Tyr | Val | Glu | Arg 460 | Ile | Glu | Glu | Leu |
| Val 465 | Gly | Val | Pro | Val | His 470 | Tyr | Ile | Gly | Val | Gly 475 | Pro | Gly | Arg | Asp | Ala 480 |
| Leu | Ile | Tyr | Lys |     |     |     |     |     |     |     |     |     |     |     |     |